United States Patent
Oleksy

(10) Patent No.: US 9,725,379 B2
(45) Date of Patent: Aug. 8, 2017

(54) METHOD FOR REDUCING ENERGY CONSUMPTION IN A PROCESS TO PRODUCE STYRENE VIA DEHYDROGENATION OF ETHYLBENZENE

(75) Inventor: Slawomir A. Oleksy, Billerica, MA (US)

(73) Assignee: Technip Process Technology, Inc., Houston, TX (US)

( * ) Notice: Subject to any disclaimer, the term of this patent is extended or adjusted under 35 U.S.C. 154(b) by 2 days.

(21) Appl. No.: 14/424,184

(22) PCT Filed: Aug. 30, 2012

(86) PCT No.: PCT/US2012/053100
§ 371 (c)(1),
(2), (4) Date: Feb. 26, 2015

(87) PCT Pub. No.: WO2014/035398
PCT Pub. Date: Mar. 6, 2014

(65) Prior Publication Data
US 2015/0210613 A1    Jul. 30, 2015

(51) Int. Cl.
*C07C 5/327*    (2006.01)
*C07C 5/32*    (2006.01)
(Continued)

(52) U.S. Cl.
CPC ............ *C07C 5/333* (2013.01); *B01J 8/0457* (2013.01); *B01J 19/245* (2013.01); *F28D 7/1607* (2013.01); *F28F 9/26* (2013.01); *B01J 8/0496* (2013.01); *B01J 2208/0053* (2013.01); *B01J 2208/00176* (2013.01); *B01J 2219/00103* (2013.01); *B01J 2219/24* (2013.01);
(Continued)

(58) Field of Classification Search
CPC .... C07C 5/327; C07C 5/32; B01J 8/04; B01J 8/02
USPC ......... 585/440, 441, 911, 920; 422/188, 198
See application file for complete search history.

(56) References Cited

U.S. PATENT DOCUMENTS 4,628,136 A    12/1986 Sardina
4,695,664 A    9/1987 Whittle
(Continued)

OTHER PUBLICATIONS

PCT Notification of Transmittal of the International Search Report and the Written Opinion of the International Searching Authority, or the Declaration dated Nov. 2, 2012 corresponding to PCT/US2012/053100 (13 pages).

(Continued)

*Primary Examiner* — Thuan D Dang
(74) *Attorney, Agent, or Firm* — Locke Lord LLP; Alan B. Clement; Peter J. Fallon

(57) ABSTRACT

The present invention is directed to improved methods and systems for increasing the efficiency of a dehydrogenation section of an alkenyl aromatic hydrocarbon production facility, wherein an alkyl aromatic hydrocarbon, such as ethylbenzene, is dehydrogenated to produce an alkenyl aromatic hydrocarbon, such as styrene. The disclosed methods are more energy-efficient and cost effective than currently known methods for manufacturing styrene. The methods and systems advantageously utilize multiple reheat exchangers arranged in a series and/or parallel configuration that result in an energy consumption reduction and, consequently, a utility cost savings, as well as a reduction in styrene manufacturing plant investment costs.

42 Claims, 5 Drawing Sheets

(51) Int. Cl.
*B01J 8/04* (2006.01)
*B01J 8/02* (2006.01)
*C07C 5/333* (2006.01)
*F28D 7/16* (2006.01)
*F28F 9/26* (2006.01)
*B01J 19/24* (2006.01)
*F28D 21/00* (2006.01)

(52) U.S. Cl.
CPC .. *F28D 21/0001* (2013.01); *F28D 2021/0022* (2013.01); *Y02P 20/124* (2015.11)

(56) References Cited

U.S. PATENT DOCUMENTS

| | | |
|---|---|---|
| 5,196,632 A | 3/1993 | Larsen et al. |
| 7,922,980 B2 | 4/2011 | Oleksy et al. |
| 8,084,660 B2 | 12/2011 | Welch et al. |
| 2009/0264692 A1 | 10/2009 | Welch et al. |
| 2010/0240940 A1 | 9/2010 | Wilcox et al. |

OTHER PUBLICATIONS

Walas, Stanley M,, "Chemical Process Equipment," (2009), p. 172.

METHOD FOR REDUCING ENERGY CONSUMPTION IN A PROCESS TO PRODUCE STYRENE VIA DEHYDROGENATION OF ETHYLBENZENE

FIELD OF INVENTION

The present invention is directed to improved methods and systems for the production of styrene via dehydrogenation of ethylbenzene, which are more energy-efficient and cost effective than currently known methods for manufacturing styrene. These methods and systems, thus, very advantageously result in an energy consumption reduction and, consequently, a utility cost savings, as well as a reduction in styrene manufacturing plant investment costs, in comparison with the current technology practiced in the industry.

BACKGROUND

Styrene is a basic building block for the manufacture of a broad range of materials. It is used to make polystyrene, acrylonitrile-butadiene-styrene, polyester resins, synthetic rubber, and a host of other products.

Production of styrene by dehydrogenation of ethylbenzene (EB) is commonly conducted by mixing ethylbenzene with steam and passing the mixture through a dehydrogenation catalyst-packed bed at elevated temperature (600-650° C. at the inlet). Steam is used as the diluent gas in the dehydrogenation reaction system to supply heat needed for the endothermic reaction of ethylbenzene to styrene (SM).

The steam used as the diluent has several other functions, e.g., it supplies the heat necessary for dehydrogenation, reduces the partial pressure of the reactants, and removes carbon on the catalyst as carbon monoxide, which is subsequently converted to carbon dioxide via the water gas shift reaction. It is difficult to recover the heat not used in the reaction from the steam and a huge amount of heat is left unrecovered when steam is used in large volume. The reduction of the amount of steam used in the dehydrogenation of ethylbenzene is a greatly desired benefit to process economy and several attempts have been made to achieve this end.

Current methods for the production of styrene via dehydrogenation of ethylbenzene utilize not less than 0.8 kg of steam per kg of ethylbenzene to bring the reactor feed to the required temperature, and to reheat the effluent between reactors, which is needed because the dehydrogenation of ethylbenzene is highly endothermic. This minimum amount of steam is necessary to keep steam temperature below 899° C., which is the maximum allowable temperature for the standard materials, such as Alloy 800H, used for fabrication of high temperature process equipment and transfer lines. Reducing steam/ethylbenzene ratio to less than 0.8 kg/kg molar would require use of very expensive alloys, which are unproven in the styrene service.

Alternate methods for avoiding high steam temperature in processes for producing styrene via dehydrogenation of ethylbenzene are known in the art. For example, U.S. Pat. No. 8,084,660 discloses a method for increasing the efficiency and/or expanding the capacity of a new or existing dehydrogenation section of a styrene plant by adding a direct heating unit to the dehydrogenation section having a reheater. The direct heating unit is positioned before or after the reactor, and the direct heating unit and reheater are operated in a parallel arrangement with respect to each other. The reactor effluent is diverted to both the direct heating unit and the reheater for heating. Operating the dehydrogenation section with an added direct heating unit provides energy savings, as compared to operating a dehydrogenation section with only a reheater.

U.S. Patent Application Publication No. 2010/0240940 discloses a method for the production of styrene by the catalytic dehydrogenation of ethylbenzene employing diluent steam at a steam to oil ratio that can be 1.0 or below. The method utilizes steam temperatures at the outlet of the steam superheater below those that would require the use of special and costly metallurgy in the high temperature process equipment. Moreover, this disclosure relies on the idea of increasing the flow of heating steam through the system without actually using more steam. This is accomplished by recirculating a portion of the heating steam by means of a compressor or a steam ejector. The compressor option seems to be less favored by the inventors, presumably due to the high cost and questionable reliability of rotary equipment operating at temperatures in excess of 600° C. The steam ejector option requires that the make-up heating steam be supplied at high pressure, which is not feasible and/or economic in a scenario where ethylbenzene and styrene production facilities are integrated; given that the ethylbenzene process produces large amounts of low pressure steam, for which the styrene process provides an outlet. This is true for the vast majority of styrene produced via dehydrogenation of ethylbenzene today.

For economic reasons there remains a need in the industry for methods and systems which can produce styrene via dehydrogenation of ethylbenzene utilizing less than about 0.8 kg of steam per kg of ethylbenzene.

SUMMARY OF THE INVENTION

The present invention is directed to a method for increasing the efficiency of a dehydrogenation section of an alkenyl aromatic hydrocarbon production facility that utilizes heating steam and feed steam. The dehydrogenation section is for dehydrogenating alkyl aromatic hydrocarbons to alkenyl aromatic hydrocarbons. The method comprises at least a first and a second dehydrogenation reactor, a feed stream comprising the alkyl aromatic hydrocarbons, wherein the first reactor effluent is heated in two or more reheat exchangers arranged in a series or parallel configuration with respect to each other. The two or more reheat exchangers are located between the first and the second reactor, and each reheat exchanger is provided with an independent stream of superheated steam, with the conditions: (a) that the steam flow rate of superheated steam to the two or more reheat exchangers is equal to or less than the steam flow rate of superheated steam to a single-reheat exchanger in an equivalent dehydrogenation section for dehydrogenating alkyl aromatic hydrocarbons to alkenyl aromatic hydrocarbons; and (b) that the temperature of the superheated steam to the two or more reheat exchangers is equal to or less than the temperature of superheated steam required by the single-reheat exchanger.

According to another embodiment, the invention is directed to a method for increasing the efficiency of a dehydrogenation section of an alkenyl aromatic hydrocarbon production facility that utilizes heating steam and feed steam. The dehydrogenation section is for dehydrogenating alkyl aromatic hydrocarbons to alkenyl aromatic hydrocarbons. The method comprises at least a first and a second dehydrogenation reactor, a feed stream comprising the alkyl aromatic hydrocarbons, wherein the first reactor effluent is heated in two or more reheat exchangers arranged in a series or parallel configuration with respect to each other. The reheat exchangers are located between the first and second reactors, and each reheat exchanger is provided with an independent stream of superheated steam, such that the inlet temperature of the superheated steam provided to the reheat exchangers is less than the inlet temperature of superheated steam required for a single-reheat exchanger that provides the same total reheat exchanger duty as the two or more reheat exchangers.

According to another embodiment, the invention is directed to a method for increasing the efficiency of a dehydrogenation section of an alkenyl aromatic hydrocarbon production facility. The dehydrogenation section is for dehydrogenating alkyl aromatic hydrocarbons to alkenyl aromatic hydrocarbons. The method comprises providing at least a first and a second dehydrogenation reactor, a feed stream comprising said alkyl aromatic hydrocarbons, wherein the first reactor effluent is heated in two or more reheat exchangers arranged in a series with respect to each other, the two or more reheat exchangers are located between the first and the second reactor, and each reheat exchanger is provided with an independent stream of superheated steam, wherein (a) the ratio of heating steam to ethylbenzene is equal to or less than the ratio of heating steam to ethylbenzene in a single-reheat exchanger of an equivalent dehydrogenation section for dehydrogenating alkyl aromatic hydrocarbons to alkenyl aromatic hydrocarbons; and (b) the temperature of the heating steam supplied to each of the two or more reheat exchangers is equal to or less than the temperature of heating steam supplied to a single-reheat exchanger that provides the same total reheat duty.

According to another embodiment, the invention is directed to a system for increasing the efficiency of a dehydrogenation section of an alkenyl aromatic hydrocarbon production facility that utilizes heating steam and feed steam. The dehydrogenation section dehydrogenates alkyl aromatic hydrocarbons to alkenyl aromatic hydrocarbons. The system comprises a first dehydrogenation reactor and a second dehydrogenation reactor R1 and R2, wherein the effluent from the first reactor R1 is reheated in two or more reheat exchangers HB1 and HB2 arranged in a series or parallel configuration with respect to each other, the first reheat exchanger HB1 in fluid communication with the first reactor R1 and the second reheat exchanger HB2 is in fluid communication with the second reactor R2, and each reheat exchanger HB1 and HB2 is provided with an independent stream of superheated steam, such that the inlet temperature of the superheated steam provided to the reheat exchangers HB1 and HB2 is less than the inlet temperature of the superheated steam required for a single-reheat exchanger HB that provides the same total reheat exchanger duty as the two or more reheat exchangers.

According to yet another embodiment, the invention is directed to a system for increasing the efficiency of a dehydrogenation section of an alkenyl aromatic hydrocarbon production facility that utilizes heating steam and feed steam. The dehydrogenation section dehydrogenates alkyl aromatic hydrocarbons to alkenyl aromatic hydrocarbons. The system comprises at least a first dehydrogenation reactor and a second dehydrogenation reactor R1 and R2 for receiving a feed stream comprising the alkyl aromatic hydrocarbons. The effluent from the first reactor R1 is reheated in two or more reheat exchangers HB1 and HB2 arranged in a series or parallel configuration with respect to each other and located between the first and second reactors R1 and R2, the first reheat exchanger HB1 in fluid communication with the first reactor R1 and the second reheat exchanger HB2 is in fluid communication with the second reactor R2, and each reheat exchanger HB1 and HB2 is provided with an independent stream of superheated steam, with the conditions: (a) that the steam flow rate of superheated steam to the two or more reheat exchangers HB1 and HB2 is equal to or less than the steam flow rate of superheated steam to a single-reheat HB exchanger in an equivalent dehydrogenation section for dehydrogenating alkyl aromatic hydrocarbons to alkenyl aromatic hydrocarbons; and (b) that the temperature of the superheated steam to the two or more reheat exchangers HB1 and HB2 is equal to or less than the temperature of superheated steam required by the single-reheat exchanger HB.

Significantly, the claimed methods and systems provide for a reduction in heating steam flow rate while not requiring the use of expensive alloys in the fabrication of reheat exchangers required for the production of styrene via dehydrogenation of ethylbenzene.

The improved systems and methods disclosed herein are substantial in terms of their economic impact, e.g., up to a 50% reduction in the amount of steam usage, and up to 25% reduction in the amount of fuel used in the reactor section, compared to the industry standard. Just as importantly, these improvements do not require fundamental changes to the process.

BRIEF DESCRIPTION OF THE SEVERAL
VIEWS OF THE DRAWINGS

DETAILED DESCRIPTION OF PREFERRED
EMBODIMENT(S)

The process and system of the instant invention generally comprises a reduction in the amount of steam and corresponding energy required for heating the reactants in the dehydrogenation section of an alkenyl aromatic hydrocarbon production facility (e.g., a styrene plant).

Figure 2:
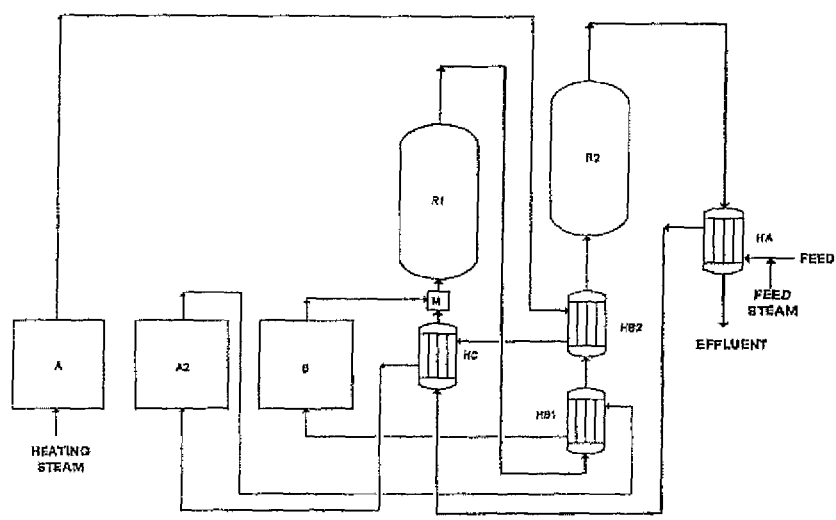
FIG. 2 is a schematic flow diagram of a non-limiting embodiment of a system having a reactor feed preheat exchanger and two or more reheat exchangers arranged in a series for use in the method herein.
Figure 3:
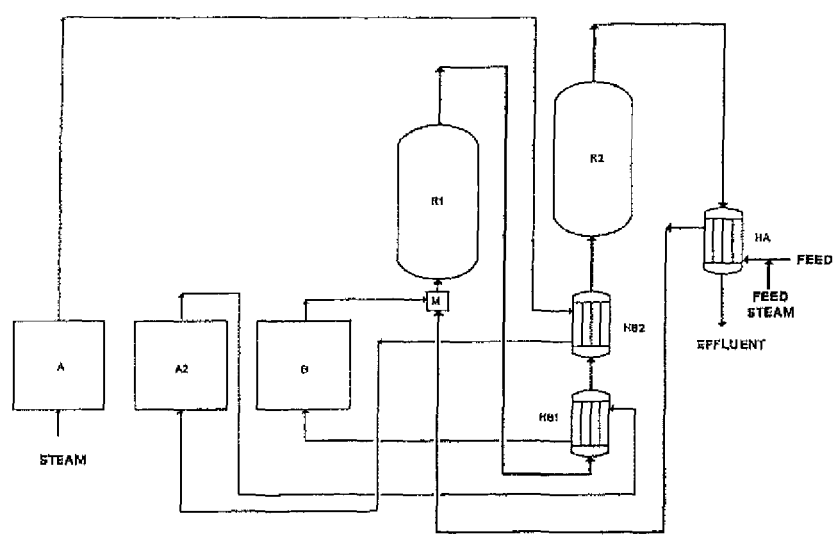
FIG. 3 is a schematic flow diagram of a non-limiting embodiment of a system having two or more reheat exchangers arranged in a series for use in the method herein.

According to an embodiment of the invention a reduction in the amount of steam required for the production of styrene via dehydrogenation of ethylbenzene is obtained by splitting the reheat exchanger duty between at least two reheat exchangers arranged in a series with respect to each other (as presented in FIGS. 2 and 3). According to another embodiment of the invention a reduction in the amount of steam required for the production of styrene via dehydrogenation of ethylbenzene is obtained by splitting the reheat exchanger duty between at least two reheat exchangers arranged in a parallel configuration with respect to each other (as presented in FIG. 5). Further, each reheat exchanger has an independent source of superheated steam. The two or more reheat exchanger bundles can be housed in separate shells (as presented in FIGS. 2 and 3), or in a single shell divided by a common channel (as presented in FIG. 4a).

A typical reheat exchanger used in the process of dehydrogenating an alkyl aromatic hydrocarbon, such as ethylbenzene, is a shell-and-tube type, having a tube bundle (i.e., a plurality of independent, unconnected tubes) held in place by tubesheets at either end, and wherein the shell side fluid, for example, superheated steam, is forced to flow across the tube bundle by means of a plurality of baffles. For purposes of this disclosure, typical reheat exchangers used in prior art systems and apparatus for dehydrogenating alkyl aromatic hydrocarbons to alkenyl aromatic hydrocarbons will be designated as single-reheat exchangers.

Figure 4:
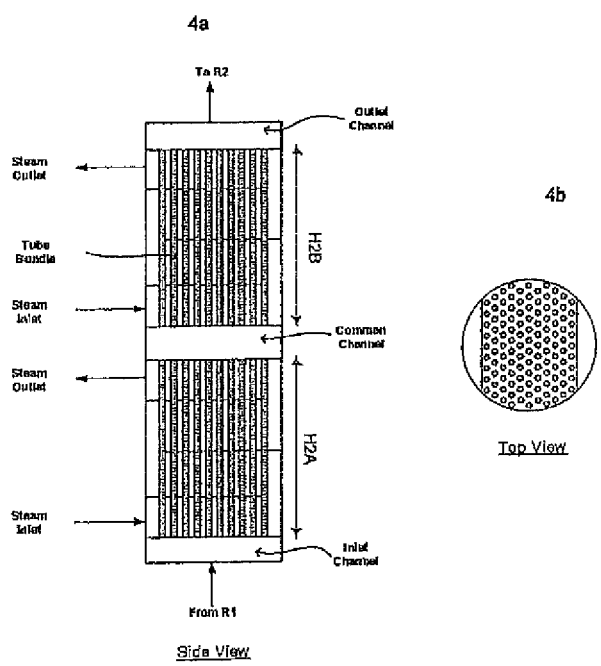
FIG. 4a is an illustration of a stacked two or more reheat exchanger.
FIG. 4b is a top view of the stacked two or more reheat exchanger.

However, in the methods and systems of the present inventions, the two or more reheat exchangers arranged in a series or parallel configuration with respect to each other, can be free-standing units or can be aligned in a radially symmetrical stack and connected to one another by empty cylindrical channels, as illustrated in FIG. 4. The stacked exchanger arrangement is preferred over a series of free-standing exchangers. The adjacent shells in an exchanger stack may or may not have the same diameter, although using the same diameter for all the shells and channels is preferred.

It will be understood by those skilled in the art that the total reheat exchanger duty is divided between the presently claimed two or more reheat exchangers arranged in a series or a parallel configuration with respect to each other, and each reheat exchanger is supplied by an independent source of superheated steam.

Alternatives to the features of the aforementioned two or more reheat exchanger arranged in a series or parallel configuration with respect to each other, such as same shell double segmental heat exchangers, and separate shells are merely illustrative of the best modes of carrying out the invention, and which are susceptible of modification of form, size, arrangement of parts and details of operation.

According to another embodiment of the invention a further reduction in the amount of steam required for the production of styrene via dehydrogenation of ethylbenzene is obtained by the inclusion of a reactor feed preheat exchanger that extracts additional heat from steam from the two or more reheat exchangers arranged in a series or parallel configuration with respect to each other that in prior art usually goes from a single-reheat exchanger directly to a steam superheater. The reactor feed preheat exchanger is a shell-and-tube type, similar in concept to the reheat exchanger described herein, with feed stream on the tube side and the heating steam on the shell side. Other reactor feed preheat exchanger designs are contemplated, however, the shell-and-tube type is preferred.

The temperature of the steam that must be supplied to the reheat exchanger in order to reheat the reactor effluent is given by the following relationship:

$$T_S = T_R + \alpha + \frac{Q}{F_S \cdot c_{PS}}$$

Ts is the temperature of the steam supplied to the reheat exchanger inlet, $T_R$ is the temperature of the reactor effluent entering the reheat exchanger, $F_S$ is the steam flow rate of steam passing through the reheat exchanger. The steam flow rate, i.e., $F_S$, represents the amount of steam as measured in units of mass/time. Q is reheat exchanger duty (i.e., enthalpy change per unit time across the reheat exchanger), $C_{PS}$ is the average heat capacity of steam at the inlet and outlet of the reheat exchanger, and α is the cold end approach (i.e., the temperature difference between the steam leaving the reheat exchanger and the reactor effluent entering the reheat exchanger), which is related to the size of the reheat exchanger (i.e., the larger the reheat exchanger, the smaller the α, with α approaching zero for an infinitely large reheat exchanger).

As can be seen from the above-referenced relationship, the required steam inlet temperature (Ts) increases with decreasing amount of heating steam $F_S$. Equally importantly, the inlet temperature (Ts) decreases as the reheat exchanger duty (Q) is reduced. Thus, by splitting the total reheat exchanger duty of the claimed process into two parts, the required steam inlet temperature (Ts) to each individual reheat exchanger of the two or more reheat exchangers operating in series with respect to each other is reduced compared with the steam inlet temperature required for a single-reheat exchanger that delivers the same reheat exchanger duty.

The reheat exchanger "duty" as defined herein is the amount of heat (i.e., thermal energy) transferred per unit time (e.g., kcal/hr, BTU/hr, Megawatt).

Figure 1:
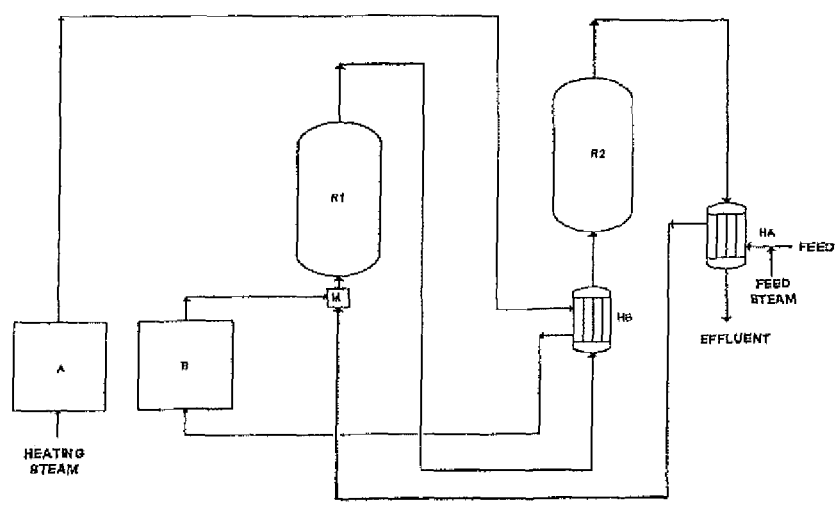
FIG. 1 is a schematic flow diagram of a system and process for the production of styrene via dehydrogenation from ethylbenzene, as seen in the prior art.
Figure 5:
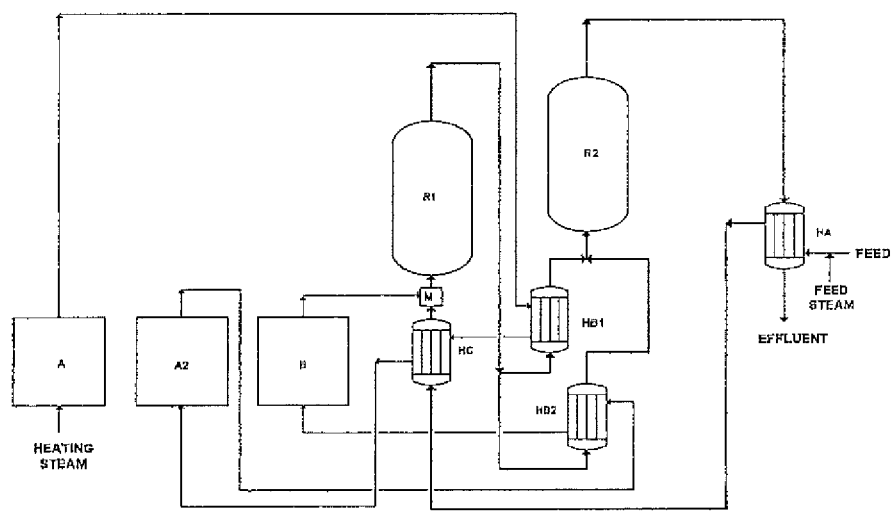
FIG. 5 is a schematic flow diagram of a non-limiting embodiment of a system having a reactor feed preheat exchanger and two or more reheat exchangers arranged in a parallel configuration for use in the method herein.

FIG. 1 presents a typical schematic flow diagram of a system and process for the production of styrene via dehydrogenation from ethylbenzene, whereas FIGS. 2, 3 and 5 are schematic flow diagrams of a non-limiting embodiments of an improved system for use in the methods and systems described herein.

The reaction takes place in a series of two reactors with an intermediate reheating step. Reactor feed, containing ethylbenzene and feed steam at a weight ratio of steam to ethylbenzene of between 0.1 and 0.6, is heated with the effluent from the second reactor RX2 in the feed-effluent heat exchanger HA, see for example, FIGS. 1-3. Feed-effluent heat exchanger HA acts as a preheater and heats the feed stream. The feed stream is mixed in a mixing vessel M with additional steam that is heated in superheater B (see FIGS. 1-3, and 5) to a temperature sufficiently high to bring the resulting mixture to proper reactor inlet temperature, typically about 600 to about 650° C. For illustrative purposes steam used to help heat the feed from feed-effluent heat exchanger HA (i.e., downstream steam) is called heating steam. And the steam added to the feed, i.e., ethylbenzene, upstream of feed-effluent heat exchanger HA (i.e., upstream steam) will be referred to as feed steam.

In FIG. 1, heating steam is first heated in the primary superheater A. From there it is directed to the single-reheat exchanger HB, where it gives up part of its heat to the reactor effluent, prior to the latter entering the second reactor R2.

In the current state of the art process, i.e., FIG. 1, heating steam leaving the reheat exchanger HB flows directly to superheater B, where it is heated up again prior to being added to the to the first reactor R1 feed. In the improved process, for example, as presented in FIG. 2, the steam leaving the reheat exchanger HB2 goes through an intermediate reactor feed preheat exchanger HC, giving up part of its heat to the reactor feed—and thereby heating the feed—prior to the latter being mixed with the heating steam in the mixing vessel M. This reduces the temperature to which the heating steam has to be heated in superheater B, or reduces the amount of heating steam required at the same B outlet temperature.

While it is true that the reactor feed preheat exchanger HC of FIG. 2 could be included in the current scheme, i.e., FIG. 1, without the need to add a second reheat exchanger and a third steam superheater (i.e., A2), such an exchanger would be very inefficient, because the steam temperature leaving the reheat exchanger HB in the process practiced currently is only slightly higher than the temperature of the reactor feed leaving the feed-effluent heat exchanger HA. On the other hand, in the improved process scheme of FIG. 2 the steam leaving the second reheat exchanger HB2 is at a much higher temperature, since only a portion of the reheat exchanger duty is done in this reheat exchanger. This makes it possible to heat the reactor feed to a higher temperature, prior to it being added to the mixing vessel M. The reactor feed preheat exchanger HC can be located either upstream of the mixing vessel M (as shown in FIG. 2) or downstream of it, with the former of these configurations preferred over the latter. Similarly, the reactor feed preheat exchanger HC can receive steam from either of the two reheat exchangers, i.e., HB1 and HB2, the preferred choice depends on which of them has a higher steam outlet temperature. Finally, the first steam superheater A2 can deliver superheated steam to either the first reheat exchanger HB1 (as depicted in FIGS. 2 and 3) or to the second reheat exchange HB2. The former configuration is preferred, because it results in the smallest combined size of the two reheat exchangers.

In the improved process presented in FIG. 2, the heating steam leaving the reactor feed preheat exchanger HC is directed to the steam superheater A2, where it is reheated, before being sent to the first reheat exchanger HB1, where the first reactor R1 effluent is heated to an intermediate temperature between that of the first reactor outlet and second reactor R2 inlet. After leaving the first reheat exchanger HB1, the heating steam is directed to superheater B.

Typically, a single-reheat exchanger as known in the art would be a shell-and-tube type having a tube bundle, as more fully described herein above. FIG. 4a, however, provides an illustration of the two or more reheat exchanger as contemplated herein. The two or more heat exchanger can be shell-and-tube type, and can consist of separate tube bundles housed in cylindrical shells. The two or more reheat exchanger can be free standing, or can be arranged in a radially symmetrical stack and connected to one another by empty cylindrical channels (i.e., not containing tubes). The stacked exchanger arrangement is preferred over a series of free-standing exchangers. The adjacent shells in an exchanger stack may or may not have the same diameter, although using the same diameter for all the shells and channels is preferred. Whether the reheat exchangers are housed in separate shells, a single shell divided by a common channel, stacked, free-standing, or a combination thereof, each reheat exchanger in a series or parallel configuration has an independent source of superheated steam. Moreover, each reheat exchanger can have different steam flow rate, which can be accomplished, for example, by adding more heating steam just upstream of superheater A2, or by bypassing steam around one of the two or more reheat exchangers in a series or parallel configuration with each other. In essence, the steam flow rate to each of the two or more reheat exchangers may, or may not be the same.

It will be understood by those skilled in the art that additional heating steam can be introduced to dehydrogenation section of a styrene plant at one or more points, for example, between the inlet of the second superheater (i.e., A2) and the inlet of the first reactor.

FIG. 4b is a top-view illustration of merely one of the tube arrangements of the stacked two or more reheat exchangers contemplated herein. Those skilled in the art may adapt other tube arrangements to be used in the invention.

Example 1A

Example 1A illustrates the conditions in current state-of-the art unoptimized process.

Ethylbenzene feed is mixed with feed steam (i.e., upstream steam) of feed-effluent exchanger HA. The weight ratio of feed steam to ethylbenzene feed is 0.2. The feed mixture is heated to 550° C. on the shell side of HA with the effluent from R2, which enters HA at a temperature of 588° C.

Downstream of HA, the feed mixture is combined with heating steam (i.e., downstream steam) that is heated in B to a temperature of 826° C. The amount of heating steam is equivalent to 0.8 kg per kg of ethylbenzene feed. The resulting final feed mixture enters R1 at a temperature of 650° C. A portion of the ethylbenzene is converted to styrene and other byproducts in R1, and the resulting effluent leaves R1 at a temperature of 561° C. It is subsequently reheated to a temperature of 650° C. in a single-reheat exchanger HB. Heating steam from superheater A enters the reheat exchanger at a temperature of 850° C. By heat balance, the resulting heating steam outlet temperature is 607° C. The heating steam is then directed to superheater B.

The size of the reheat exchangers HA and HB in this example was selected, so that the steam outlet temperature from superheaters A and B does not exceed the maximum allowable temperature for Alloy 800H (899° C. according to code). This alloy has been utilized extensively for fabrication of high temperature equipment for the production of styrene via dehydrogenation of ethylbenzene.

Example 1B

Example 1B, shows the impact of implementing two out of the three aforementioned embodiments of the present invention, in particular, the inclusion of at least two reheat exchangers in a series with respect to one another and a third superheater. The system for use in the method of performing Example 1B is illustrated in FIG. 3.

The flow rates of ethylbenzene, feed steam and heating steam are the same as in Example 1, as are the reactor temperatures (inlet and outlet) and the temperature of ethylbenzene and feed steam leaving reheat exchanger HA.

In contrast to Example 1A, the reheat exchanger duty of Example 1B is divided between two reheat exchangers HB1 and HB2 arranged in a series with respect to one another, with a total surface area identical to the surface area of the single-reheat exchanger HB in Example 1A. In addition, Example B1 is based on the condition that the steam flow rate (Fs) for the two or more reheat exchangers arranged in a series is the same as for a single-reheat exchanger.

However, the disclosed process contemplates situations where the steam flow rate (Fs) is reduced when the combined duty of the two or more reheat exchangers arranged in a series is the same or greater than a single-reheat exchanger. In this scenario, the two or more reheat exchangers in a series require less superheated steam than the amount of superheated steam that would be required by a single-reheat exchanger operating at the same temperature.

In Example 1B the area is divided equally between the first reheat exchanger (HB1) and the second reheat exchanger (HB2), and the steam temperature to reheat exchanger HB1 is adjusted such that 50% of total duty is performed in this exchanger. It should be noted that it is not a requirement of the process disclosed herein that the two reheat exchangers be the same size, or that they perform an equal portion of the overall duty.

Given the available surface area in reheat exchanger HB1, the required steam inlet temperature (supplied by A2) is 756° C. Steam exits HB1 at a temperature 633° C., and the cold end temperature approach α in this bundle is 72° C. (α is 46° C. in the single bundle reheater of Example 1A).

The reactor effluent leaves HB1 at a temperature of 606° C. and is reheated in HB2 to 650° C. using steam that originates in superheater A. The required steam inlet temperature in HB2 is 799° C., and steam exits HB2 at a temperature of 678° (α is 72° C., same as in HB1. Since there is no need for a reactor feed superheater HC (the temperature at the outlet of B is the same as in Example 1A, and is well within the limits of conventional apparatus materials, such as, Alloy 800H), steam exiting HB2 is sent directly to superheater A2.

As can be seen, the maximum steam temperature required for reheating the reactor effluent is substantially lower than in the conventional process of Example 1A (51° C. lower in HB2, and 94° C. in HB1). Furthermore, the temperature is low enough to allow use of less expensive stainless steel, for example 304H, in place of Alloy 800H, reducing the overall investment cost.

Example 2a

The process configuration in Example 2A is identical to Example 1A (see FIG. 1). Ethylbenzene flow rate, reactor temperatures and the temperature of ethylbenzene and steam exiting HA are also the same, as is the total amount of steam used. The key difference is that the weight ratio of feed steam to ethylbenzene is increased from 0.2 to 0.5, and the ratio of heating steam to ethylbenzene is reduced to from 0.8 to 0.5, however, the overall steam to ethylbenzene ratio remains at 1.0. These ratios are representative of a heat recovery system being present upstream of HA, wherein a mixture of ethylbenzene and water is vaporized azeotropically using the heat contained in the overhead vapor from the EB/SM splitter column that would normally be rejected to cooling water or air. In effect, this type of scheme has the potential to reduce the net amount of steam required in the reaction section of the styrene plant by about one half.

U.S. Pat. Nos. 4,628,136 and 7,922,980, the contents of which are fully incorporated by reference herein, describe a process wherein the overhead of an ethylbenzene/styrene splitter column is used to vaporize an azeotropic mixture of ethylbenzene and water, as referred to in Examples 2A-2C and 3, herein.

With the feed steam (i.e., steam added upstream of HA) increased to 0.5 kg/kg of ethylbenzene and heating steam (i.e., steam added downstream of HA) reduced to 0.5 kg/kg ethylbenzene, the heating steam temperature required to bring the first reactor R1 inlet temperature to 650° C. is increased to 981° C., far above what can be handled with conventional Alloy 800H, which has a limit of 899° C. (as defined by API and ASME codes). Likewise, even with an infinitely large reheat exchanger, the temperature of heating steam that has to be supplied to HB is 946° C. A reheat exchanger of the same size as in Example 1A requires a steam inlet temperature of 968° C. Such high temperature would necessitate the use of very expensive alloys. It is also important to note that styrene industry has no experience with use of such alloys for large equipment and steam transfer lines. Therefore, there would be a considerable development effort required to successfully implement such a significant change to metallurgy.

Example 2B

Example 2B is identical to Example 2A (see FIG. 1), except that the ratio of heating steam (i.e., downstream steam of HA) to ethylbenzene is increased to 0.8 kg/kg of ethylbenzene, raising the overall steam to ethylbenzene ratio to 1.3 kg/kg, i.e., Reactor Steam/EB (kg/kg). Doing so reduces the superheater A and B outlet temperatures to 854° C. and 860° C., respectively, which makes it possible to use Alloy 800H, at the expense of higher energy consumption.

Example 2C

The process configuration in this example is represented by FIG. 2. The ethylbenzene and steam flow rates are the same as in Example 2A, as are reactor temperatures and the temperature of ethylbenzene and steam exiting HA.

In this example, the total surface area of the two reheat exchangers HB1 and HB2 is the same as the surface area of HB in Example 1A. In order to maximize the steam temperature entering BC more surface area is used in HB1 than in HB2, i.e., 78% and 22% of the total, respectively. By maximizing the steam temperature entering HC, a larger reduction in B steam outlet temperature is possible.

With the total area divided as above between the two reheat exchangers, reactor effluent is heated to a temperature of 619° C. in HB1, i.e., 65% of the total heat input necessary to bring the reactor effluent to 650° C. The required steam temperature at the inlet to HB1 is 849° C., well below the maximum limit of Alloy 800H. The steam inlet temperature required to heat the reactor effluent from 619° C. to 650° C. in HB2 is 853° C.

The heating steam leaving HB2 is at 718° C., which is sufficient to heat the mixture of ethylbenzene and feed steam in HC from 550° C. to 586° C. in an exchanger half the size of the reheater HB (of FIG. 1). With the ethylbenzene and feed steam entering the mixing vessel M at this temperature, the temperature of steam required to heat the overall mixture to 650° C. at the inlet of R1 is 868° C., well over 100° C. colder than in Example 2A. This could be reduced further to a minimum of 839° C., by increasing the size of HC.

Similarly, the relative sizes of the two reheat exchangers (HB1 and HB2) could be optimized to reduce overall investment cost. For example, by increasing the size of HB1 and HB2 by 40% and 25%, respectively, the former could be fabricated entirely from 304H SS, which is much less expensive than Alloy 800H. This would save investment cost, despite the increase in the combined size of HB1 and HB2.

Comparing Example 2B with Example 2C, the reheat exchanger duty in example 2C (dual-reheater, i.e., two or more reheat exchangers arranged in a series with respect to one another) is 105.8 kcal/kg EB vs. 106.7 in example 2B (single-reheater), and it is apparent that the improved process allows for a reduction in reactor steam requirements of 0.3 kg/kg of ethylbenzene, while at the same time reducing fuel consumption by about 20%.

Example 3

Current generation of ethylbenzene dehydrogenation catalysts can be operated at an overall reactor steam to ethylbenzene ratio as low as 1.0 kg/kg in a two reactor system. It is noted that lower reactor steam to ethylbenzene ratios are possible, but require three or more reactors operating in series. However, with reactor steam to ethylbenzene ratios lower than 1.0 kg/kg, catalyst activity is insufficient to provide adequate run length and to achieve economically viable raw materials consumption. With future advancements in catalysts, it may be possible to reduce the minimum reactor steam to ethylbenzene ratio to as low as 0.85 kg/kg, without adversely affecting run length or raw materials consumption.

Example 3 illustrates that the improved process of the claimed invention will make it possible to take advantage of these catalyst improvements, without the need to resort to the use of expensive and unproven metal alloys for the fabrication of critical equipment, and without losing the benefits provided by azeotropic heat recovery.

The process scheme in this example is the same as in Examples 1B (FIG. 3) and 2C (FIG. 2.). The key difference is that the ratio of heating steam (i.e., downstream steam of HA) to ethylbenzene is reduced from 0.5 to 0.4 kg/kg.

In order to keep the steam temperatures below 899° C. (i.e., the limit for Alloy 800H), the surface area of HB1 and HC is increased, while the size of HB2 is actually decreased slightly. Using the surface area of HB in Example 1A as reference, the surface area of HB1 is 0.9 (0.78 in Example 2C), that of HB2 is 0.25 (0.28 in example 2C) and that of HC is 0.75 (0.5 in Example 2C). The corresponding superheater A, A2 and B outlet temperatures are 895° C., 883° C., and 883° C., respectively.

Table 1 summarizes the key results from the examples discussed above. Q (reheat exchanger duty) has been previously described and the HB, HB1, HB2, and HC, Q data for Examples 1A-B, 2A-C, and 3 are presented in Table 1. Additionally, absorbed duty, i.e., Absorbed Q, data for the Examples are presented in Table 1. The absorbed duty is the duty (energy) absorbed by the superheated steam. The energy released by the burning of fuel to heat the steam is greater than the absorbed duty because superheaters are not 100% efficient. Since the superheater efficiency is the same for the prior art and the methods disclosed herein, it follows that the amount of fuel used is directly proportional to the total absorbed duty.

"Reactor Steam" in Table 1 refers to the sum of Heating and Feed Steam, which are described herein above. "Net Steam Required" is equal to the Reactor Steam in cases where there is no azeotropic heat recovery (i.e., Example 1). For cases where azeotropic heat recovery is present (i.e., Examples 2A-C and 3), it is equal to the Heating Steam, since the Feed Steam is considered "free."

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A method for increasing the efficiency of a dehydrogenation section of an alkenyl aromatic hydrocarbon production facility, said dehydrogenation section for dehydrogenating alkyl aromatic hydrocarbons to alkenyl aromatic hydrocarbons, said method comprising:
   providing at least a first and a second dehydrogenation reactor and
   a feed stream comprising said alkyl aromatic hydrocarbons;
   reacting the feed in the first reactor to provide a first reactor effluent;
   heating the first reactor effluent in two or more steam reheat exchangers prior to entering the second reactor, said two or more reheat exchangers being located between the first and the second reactor,
   providing each reheat exchanger with an independent stream of superheated steam; and
   reheating the steam leaving at least one of the two or more reheat exchanger prior to entering the other reheat exchanger, wherein (a) the flow rate of superheated steam to the two or more reheat exchangers is equal to or less than the steam flow rate of superheated steam required by a single-reheat exchanger in an equivalent dehydrogenation section for dehydrogenating alkyl aromatic hydrocarbons to alkenyl aromatic hydrocarbons, and (b) the temperature of the superheated steam to the two or more reheat exchangers is equal to or less than the temperature of superheated steam required by the single-reheat exchanger.

TABLE 1

|  | 1A | 1B | 2A | 2B | 2C | 3 |
|---|---|---|---|---|---|---|
| Process Scheme | Prior Art Method | Claimed Method | Prior Art Method | Prior art Method | Claimed Method | Claimed Method |
| Heating Steam/EB (kg/kg) | 0.80 | 0.80 | 0.50 | 0.80 | 0.50 | 0.40 |
| Feed Steam/EB (kg/kg) | 0.20 | 0.20 | 0.50 | 0.50 | 0.50 | 0.50 |
| Reactor Steam/EB (kg/kg) | 1.00 | 1.00 | 1.00 | 1.30 | 1.00 | 0.90 |
| Net Steam Required/EB (kg/kg) | 1.00 | 1.00 | 0.50 | 0.80 | 0.50 | 0.40 |
| Fractional EB Conversion | 0.64 | 0.64 | 0.64 | 0.64 | 0.64 | 0.64 |
| R1 Inlet Temperature (° C.) | 650 | 650 | 650 | 650 | 650 | 650 |
| R1 Outlet Temperature (° C.) | 561 | 561 | 561 | 571 | 561 | 551 |
| HB2 Tube Inlet Temp (° C.) | N/A | 606 | N/A | N/A | 619 | 612 |
| R2 Inlet Temperature (° C.) | 650 | 650 | 650 | 650 | 650 | 650 |
| R2 Outlet Temperature (° C.) | 588 | 588 | 588 | 596 | 588 | 579 |
| HA Feed Outlet Temp (° C.) | 550 | 550 | 550 | 550 | 550 | 550 |
| HC Feed Outlet Temp (° C.) | NA | NA | NA | NA | 586 | 588 |
| A Inlet Temp (° C.) | 155 | 155 | 155 | 155 | 155 | 155 |
| A Outlet Temp (° C.) | 850 | 799 | 968 | 854 | 853 | 895 |
| A2 Inlet Temp (° C.) | N/A | 678 | N/A | N/A | 597 | 568 |
| A2 Outlet Temp (° C.) | N/A | 756 | N/A | N/A | 849 | 883 |
| HC Steam Inlet Temp (° C.) | N/A | N/A | N/A | N/A | 718 | 730 |
| B Inlet Temp (° C.) | 607 | 633 | 585 | 609 | 596 | 567 |
| B Outlet Temp (° C.) | 826 | 826 | 981 | 860 | 868 | 883 |
| A Absorbed Q (kcal/kg EB) | 288 | 265 | 214 | 289 | 181 | 154 |
| A2 Absorbed Q (kcal/kg EB) | N/A | 84 | N/A | N/A | 74 | 69 |
| B Absorbed Q (kcal/kg EB) | 95 | 34 | 109 | 110 | 69 | 68 |
| Total Absorbed Q (kcal/kg EB) | 383 | 383 | 323 | 399 | 323 | 291 |
| HB Q (kcal/kg) | 106 | — | 106 | 107 | — | — |
| HB1 Q (kcal/kg) | — | 53 | — | — | 69 | 69 |
| HB2 Q (kcal/kg) | — | 53 | — | — | 37 | 37 |
| HC Q (kcal/kg) | — | — | — | — | 32 | 34 |

2. The method of claim 1, wherein the independent stream of superheated steam to each reheat exchanger is provided by an independent superheater.

3. The method of claim 1, wherein the feed stream is heated by the second reactor effluent in a feed-effluent heat exchanger prior to entering the first reactor.

4. The method of claim 3, further comprising feed steam that is mixed with the feed stream upstream of said feed-effluent heat exchanger.

5. The method of claim 1, wherein said dehydrogenation section comprises at least 3 independent superheaters.

6. The method of claim 1, wherein the alkyl aromatic hydrocarbon is ethylbenzene.

7. The method of claim 1, wherein the alkenyl aromatic hydrocarbon is styrene.

8. The method of claim 1, wherein the independent streams of superheated steam have a temperature that is not greater than the maximum allowable operating temperature for Alloy 80014 as defined by the applicable ASME and API codes.

9. The method of claim 1, wherein the independent streams of superheated steam have a temperature that is not greater than 899° C.

10. The method of claim 6, wherein the weight ratio of heating steam to ethylbenzene is in the range of 0.40 to 0.80.

11. The method of claim 6, wherein weight the ratio of feed steam to ethylbenzene is between 0.10 and 0.60.

12. A method for increasing the efficiency of a dehydrogenation section of an alkenyl aromatic hydrocarbon production facility, said dehydrogenation section for dehydrogenating alkyl aromatic hydrocarbons to alkenyl aromatic hydrocarbons, said method comprising:
providing at least a first and a second dehydrogenation reactor; and
a feed stream comprising said alkyl aromatic hydrocarbons;
reacting the feed in the first reactor to provide a first reactor effluent;
heating said first reactor effluent in two or more steam reheat exchangers prior to entering the second reactor, said two or more reheat exchangers being located between the first and the second reactor,
providing each reheat exchanger with an independent stream of superheated steam; and
reheating the steam leaving at least one of the two or more reheat exchanger prior to entering the other reheat exchanger, wherein, the inlet temperature of said superheated steam provided to the two or more reheat exchangers is less than the inlet temperature of superheated steam required far by a single-reheat exchanger that provides the same total reheat exchanger duty as the two or more reheat exchangers.

13. The method of claim 12, wherein the independent stream of superheated steam to each reheat exchanger is provided by an independent superheater.

14. The method of claim 12, wherein the feed stream is heated by the second reactor effluent in a feed-effluent heat exchanger prior to entering the first reactor.

15. The method of claim 14, further comprising feed steam that is mixed with the feed stream upstream of said feed-effluent heat exchanger.

16. The method of claim 12, wherein the alkyl aromatic hydrocarbon is ethylbenzene.

17. The method of claim 12, wherein the alkenyl aromatic hydrocarbon is styrene.

18. The method of claim 12, wherein the independent streams of superheated steam have a temperature that is not greater than the maximum allowable operating temperature for Alloy 800H as defined by the applicable ASME and API codes.

19. The method of claim 12, wherein the independent streams of superheated steam have a temperature that is not greater than 899° C.

20. The method of claim 16, wherein the weight ratio of heating steam to ethylbenzene is in the range of 0.40 to 0.80.

21. The method of claim 16, wherein weight the ratio of feed steam to ethylbenzene is between 0.10 and 0.60.

22. A system for increasing the efficiency of dehydrogenating of alkyl aromatic hydrocarbons to alkenyl aromatic hydrocarbons in a dehydrogenation section of an alkenyl aromatic hydrocarbon production facility, said system comprises a first dehydrogenation reactor and a second dehydrogenation reactor for receiving a feed stream comprising the alkyl aromatic hydrocarbons, wherein the effluent from the first reactor is reheated in two or more reheat exchangers in fluid communication with one another and located between the first and second reactor, a first reheat exchanger of the two or more reheat exchanger is in fluid communication with the first reactor and a second reheat exchanger of the two or more reheat exchanger is in fluid communication with the second reactor, and each reheat exchanger is provided with an independent stream of superheated steam and the steam leaving at least one of the two or more reheat exchanger is heat prior to entering the other reheat exchanger, wherein the inlet temperature of the superheated steam provided to the reheat exchangers is less than the inlet temperature of superheated steam required by a single-reheat exchanger that provides the same total reheat exchanger duty as the two or more reheat exchangers.

23. The system of claim 22, wherein the independent streams of superheated steam to each reheat exchanger of the two or more reheat exchangers are provided by independent superheaters.

24. The system of claim 22, wherein the feed stream is heated by the second reactor effluent in a feed-effluent heat exchanger prior to entering the first reactor.

25. The system of claim 24, further comprising feed steam that is mixed with the feed stream upstream of said feed-effluent heat exchanger.

26. The system of claim 22, wherein the alkyl aromatic hydrocarbon is ethylbenzene.

27. The system of claim 22, wherein the alkenyl aromatic hydrocarbon is styrene.

28. The system of claim 22, wherein the independent streams of superheated steam have a temperature that is not greater than the maximum allowable operating temperature for Alloy 800H as defined by the applicable ASME and API codes.

29. The system of claim 22, wherein the independent streams of superheated steam have a temperature that is not greater than 899° C.

30. The system of claim 26, wherein the weight ratio of heating steam to ethylbenzene is in the range of 0.40 to 0.80.

31. The system of claim 26, wherein weight the ratio of feed steam to ethylbenzene is between 0.10 and 0.60.

32. A system for increasing the efficiency of dehydrogenating of alkyl aromatic hydrocarbons to alkenyl aromatic hydrocarbons in a dehydrogenation section of an alkenyl aromatic hydrocarbon production facility, said system comprises a first dehydrogenation reactor and a second dehydrogenation reactor for receiving a feed stream comprising said alkyl aromatic hydrocarbons, wherein the effluent from the first reactor is reheated in two or more reheat exchangers located between the first and second reactor, a first of the two or more reheat exchanger is in fluid communication with the first reactor and a second of the two or more reheat exchanger is in fluid communication with the second reactor, and each reheat exchanger is provided with an independent stream of superheated steam and the steam leaving at least one of the two or more reheat exchanger is heat prior to entering the other reheat exchanger, wherein (a) the steam flow rate of superheated steam to the two or more reheat exchangers is equal to or less than the steam flow rate of superheated steam required by a single-reheat exchanger in an equivalent dehydrogenation section for dehydrogenating alkyl aromatic hydrocarbons to alkenyl aromatic hydrocarbons, and (b) the temperature of the superheated steam to the two or more reheat exchangers is equal to or less than the temperature of superheated steam required by the single-reheat exchanger.

33. The system of claim 32, wherein the independent streams of superheated steam to each reheat exchanger of the two or more reheat exchangers are provided by independent superheaters.

34. The system of claim 32, wherein the feed stream is heated by the second reactor effluent in a feed-effluent heat exchanger prior to entering the first reactor.

35. The system of claim 34, further comprising feed steam that is mixed with the feed stream upstream of said feed-effluent heat exchanger.

36. The system of claim 32, wherein the alkyl aromatic hydrocarbon is ethylbenzene.

37. The system of claim 32, wherein the alkenyl aromatic hydrocarbon is styrene.

38. The system of claim 32, wherein the independent streams of superheated steam have a temperature that is not greater than the maximum allowable operating temperature for Alloy 800H as defined by the applicable ASME and API codes.

39. The system of claim 32, wherein the independent streams of superheated steam have a temperature that is not greater than 899° C.

40. The system of claim 36, wherein the weight ratio of heating steam to ethylbenzene is in the range of 0.40 to 0.80.

41. The system of claim 36, wherein weight the ratio of feed steam to ethylbenzene is between 0.10 and 0.60.

42. A method for increasing the efficiency of a dehydrogenation section of an alkenyl aromatic hydrocarbon production facility, said dehydrogenation section for dehydrogenating alkyl aromatic hydrocarbons to alkenyl aromatic hydrocarbons, said method comprising:
    providing at least a first and a second dehydrogenation reactor and
    a feed stream comprising said alkyl aromatic hydrocarbons;
    reacting the feed in the first reactor to provide a first reactor effluent;
    heating the first reactor effluent in two or more steam reheat exchangers prior to entering the second reactor, said two or more reheat exchangers being located between the first and the second reactor,
    providing each reheat exchanger with an independent stream of superheated steam; and
    reheating the steam leaving at least one of the two or more reheat exchanger prior to entering the other reheat exchanger, wherein (a) the ratio of heating steam to ethylbenzene is equal to or less than the ratio of heating steam to ethylbenzene required by a single-reheat exchanger of an equivalent dehydrogenation section for dehydrogenating alkyl aromatic hydrocarbons to alkenyl aromatic hydrocarbons; and (b) the temperature of the heating steam supplied to each of the two or more reheat exchangers is equal to or less than the temperature of heating steam required by a single-reheat exchanger that provides the same total reheat duty.

* * * * *